United States Patent
Matousek et al.

(10) Patent No.: US 10,040,812 B2
(45) Date of Patent: Aug. 7, 2018

(54) HYPERVALENT IODINE CF2CF2X REAGENTS AND THEIR USE

(71) Applicants: ETH Zurich, Zurich (CH); INSTITUTE OF ORGANIC CHEMISTRY AND BIOCHEMISTRY ACADEMY OF SCIENCES OF THE CZECH REPUBLIC, V.V.I, Prague (CZ)

(72) Inventors: Vaclav Matousek, Zliv (CZ); Petr Beier, Podebrad (CZ); Antonio Togni, Zurich (CH)

(73) Assignees: ETH ZURICH, Zurich (CH); INSTITUTE OF ORGANIC CHEMISTRY AND BIOCHEMISTRY ACADEMY OF SCIENCES OF THE CZECH REPUBLIC, V.V.I, Prague (CZ)

( * ) Notice: Subject to any disclaimer, the term of this patent is extended or adjusted under 35 U.S.C. 154(b) by 0 days.

(21) Appl. No.: 15/501,872

(22) PCT Filed: Aug. 3, 2015

(86) PCT No.: PCT/CH2015/000113
§ 371 (c)(1),
(2) Date: Feb. 6, 2017

(87) PCT Pub. No.: WO2016/019475
PCT Pub. Date: Feb. 11, 2016

(65) Prior Publication Data
US 2017/0233420 A1    Aug. 17, 2017

(30) Foreign Application Priority Data
Aug. 7, 2014 (EP) .................... 14180136

(51) Int. Cl.
C07D 347/00  (2006.01)
C07F 9/6561  (2006.01)
C07D 421/06  (2006.01)

(52) U.S. Cl.
CPC ........ *C07F 9/65616* (2013.01); *C07D 347/00* (2013.01); *C07D 421/06* (2013.01)

(58) Field of Classification Search
CPC .................................................. C07D 347/00
See application file for complete search history.

(56) References Cited

PUBLICATIONS

He et al. (Angewandte Chemie, International Edition (2012), 51(16), 3944-3947).*
Mizuta S. et al: "Trifluoromethylation of allylsilanes under photoredox catalysis", Organic Letters, vol. 15, No. 6, Mar. 6, 2013 (Mar. 6, 2013), pp. 1250-1253.
Zhang B. et al:"6-Trifluoromethyl-phenanthridines through radical trifluoromethylation of isonitriles", Angewandte Chemie International Edition, vol. 52, No. 41, Oct. 4, 2013 (Oct. 4, 2013), pp. 10792-10795.
Li Y. et al: "Transition-metal-free trifluoromethylaminoxylation of alkenes", Angewandte Chemie International Edition, vol. 51, No. 33, Aug. 13, 2012 (Aug. 13, 2012),pp. 8221-8224.
Carboni A. et al: "Photoredox-induced three-component oxy-, amino-, and carbotrifluoromethylation of enecarbamates", Organic Letters, vol. 16, No. 4, Feb. 12, 2014(Feb. 12, 2014), pp. 1240-1243.

* cited by examiner

*Primary Examiner* — Bruck Kifle
(74) *Attorney, Agent, or Firm* — JMB Davis Ben-Daivd

(57) ABSTRACT

A hypervalent iodine of formula (I) or formula (II) wherein R is a nucleophile and a method for their production is described. Such compounds can be used for fluoroethylation of compounds carrying a reactive group. A preferred compound carrying a reactive group is cystein in any environment such as peptide targets.

17 Claims, 1 Drawing Sheet

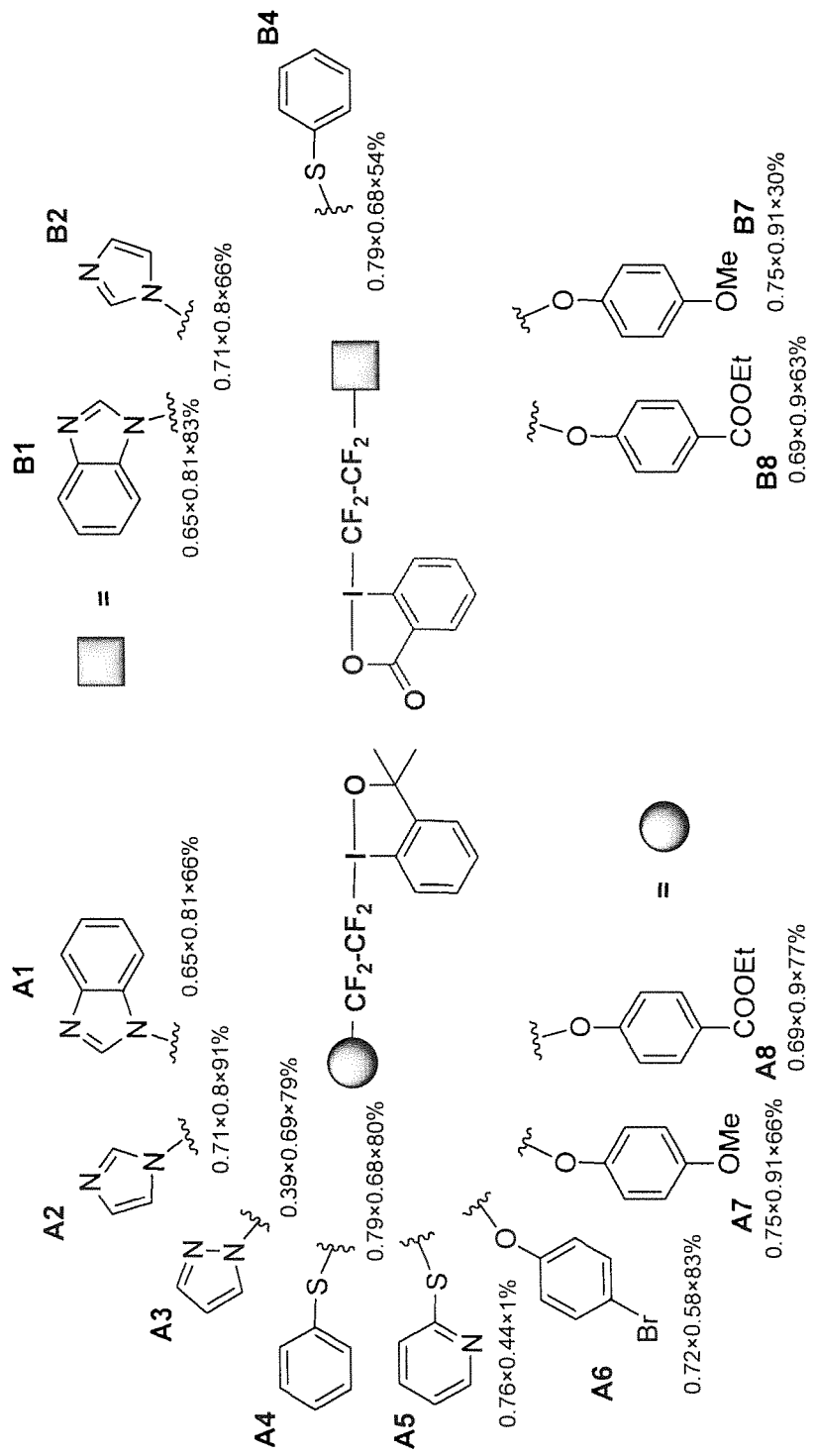

HYPERVALENT IODINE CF2CF2X REAGENTS AND THEIR USE

CROSS REFERENCES TO RELATED APPLICATIONS

This is the U.S. National Stage of International Application No. PCT/CH2015/000113 filed on Aug. 3, 2015, which was published in English under PCT Article 21(2), and which in turn claims the priority of European patent application no. 14 180 136.5, filed Aug. 7, 2014, the disclosure of which is incorporated herein by reference in its entirety.

TECHNICAL FIELD

The present invention concerns the field of fluoroalkylation by hypervalent iodine and coupling reactions using such hypervalent iodine.

BACKGROUND ART

The hypervalent cyclic $CF_3$-iodine reagents[1]

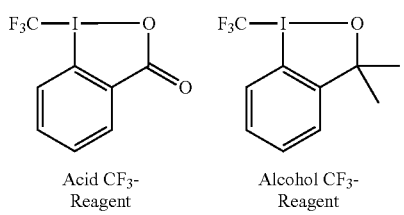

Acid $CF_3$-
Reagent

Alcohol $CF_3$-
Reagent known as Togni reagents (herein referred to as acid $CF_3$ reagent and alcohol $CF_3$ reagent) turned out to be extremely versatile donors of the formally electrophilic $CF_3$-synthon. The success story of the Togni reagents also inspired other research groups to develop other fluoroalkylated analogues of them and explore their potential in electrophilic fluoroalkylation.

In 2008, Hu et al. reported a synthesis of a related (phenylsulfonyl)difluoromethyl hypervalent iodine reagent, utilizing the Umpolung concept known from the Togni reagents. The (phenylsulfonyl)difluoromethyl trimethylsilane, which has shown competence in several examples of nucleophilic difluorosulfonylation and indirect difluoromethylation,[2] was subjected to Umpolung with acetoxyiodane to give (phenylsulfonyl)difluoromethyl hypervalent iodine reagent in good yield.[3]

In their original report, the stable alcohol $PhSO_2CF_2$-reagent could be employed in electrophilic (phenylsulfonyl)difluoromethylation of a variety of thiol substrates in up to 87% yield.

In 2012, Hu et al. demonstrated that the (phenylsulfonyl) difluoromethylation hypervalent iodine reagent can be used for electrophilic (phenylsulfonyl)difluoromethylation of α,β-unsaturated carboxylic acids in the presence of catalytic amounts of an in-situ formed copper complex. Under the applied reaction conditions, acrylate substrates underwent decarboxylation followed by phenylsulfonyldifluoromethylation.[4]

In a publication that followed very soon, the same research group could show that (β,γ-unsaturated carboxylic acids undergo decarboxylation/phenysulfonyl-difluoromethylation to give allylic phenylsulfonyl-difluoromethylated products in good yields. The resulting products could be further transformed into useful difluoromethylated and difluoromethylenated products.[5]

Apart from the (phenylsulfonyl)difluoromethylation hypervalent iodine reagent, perfluoroethyl analogue of acid $CF_3$ reagent was synthesized by Studer et al. who showcased that the resulting reagent can be used similarly as acid CF3 reagent in tandem radical fluoroalkylation/aminoxylation.[6]

Perfluoroethylation is also mentioned in further documents. Mizuta et al. disclose trifluoromethylation of allylsilanes under photoredox catalysis with an indication that also some perfluoroethylation at the allylic position was successful.[13] Zhang et al. discuss mechanistic aspects of perfluoroalkylation. In particular trifluoromethylation.[14] Carboni et al. also deal with perfluoroalkylation, in particular trifluoromethylation, of enecarbamates with one example concerning perfluoroethylaton. [15]

While the (phenylsulfonyl)difluoromethyl substituted reagent has been shown suitable for producing some trifluoromethylated and difluoromethylenated olefins, there is still a need for further fluoroalkylated products.

DISCLOSURE OF THE INVENTION

Hence, it is a general object of the invents to provide a reagent that is suitable for fluoroalkylating a broad variety of compounds and having broad applicability.

Now, in order to implement these and still further objects of the invention, which will become more readily apparent as the description proceeds, the fluoroalkylation reagent of the present invention is a hypervalent iodine of formula (I) and/or formula (II)

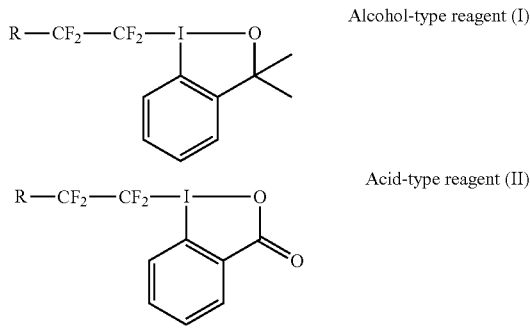

Alcohol-type reagent (I)

Acid-type reagent (II)

wherein R is a nucleophile other than fluorine or perfluoroalkyl.

Compounds of formula (I) or formula (II) with a specific R will later on be termed (specific R)-I or (specific R)-II, i.e. for e.g. R=PhS the compounds will be termed PhS-I and PhS-II.

Compounds with the basic structure

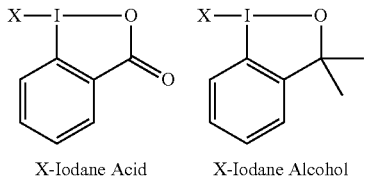

X-Iodane Acid    X-Iodane Alcohol wherein X may be any group are also termed iodanes or more specific X-iodane acid and X-iodane alcohol.

In the compounds of formula (I) or formula (II) preferred nucleophiles are selected from the group consisting of unsubstituted or substituted imidazoles, unsubstituted or substituted pyrazoles, unsubstituted or substituted benzimidazoles, unsubstituted or substituted thiophenols, unsubstituted or substituted phenols, like 4-methoxyphenols, ethyl-4-hydroxybenzoates, 4-bromophenols, unsubstituted or substituted pyridinethiols, unsubstituted or substituted 2-mercaptobenzothiazoles, potassium cyanide and diethylphosphite, more preferred imidazole, pyrazole, benzimidazole, thiophenol, 4-methoxyphenol, ethyl-4-hydroxybenzoate, 4-bromophenols, pyridine-2-thiol, 2-mercaptobenzothiazoles, potassium cyanide and diethylphosphite, even more preferred imidazole, pyrazole, benzimidazole, thiophenol, 4-methoxyphenol, ethyl-4-hydroxybenzoate, 4-bromophenols and pyridine-2-thiol.

Suitable substituents can independently from each other be small groups like halogens, linear or branched, unsubstituted or halogen substituted C1 to C4 alkyl or C1 to C4 alkenyl or C1 to C4 alkinyl or C1 to C4 alkoxy or C1 to C4 alkyl carboxylate groups. In specific cases a substituent can also be a linker or spacer coupled to a desired group such as a functional group, said linker preferably being an optionally halogen substituted aliphatic group.

In general the R listed above will be unsubstituted (i.e. the —R will not be further substituted than explicitly indicated above).

A preferred synthesis involves an intermediate compound of type R—CF$_2$—CF$_2$—SiPh$_x$(C$_1$-C$_3$-alkyl)$_{3-x}$ wherein Ph is phenyl and x is 0 to 3, preferred R—CF$_2$—CF$_2$—SiMe$_3$. This intermediate can be produced via different routes. One of these routes uses 1,2,-dibromo-1,1,2,2-tetrafluoroethane (also termed Halon 2402) that can be readily prepared but that for its ozone depleting potential is not easily commercially available in high amounts.

Starting from R—H and Br—CF$_2$—CF$_2$—Br, in a first step R—CF$_2$—CF$_2$—Br is formed, possibly via a mechanism as follows:

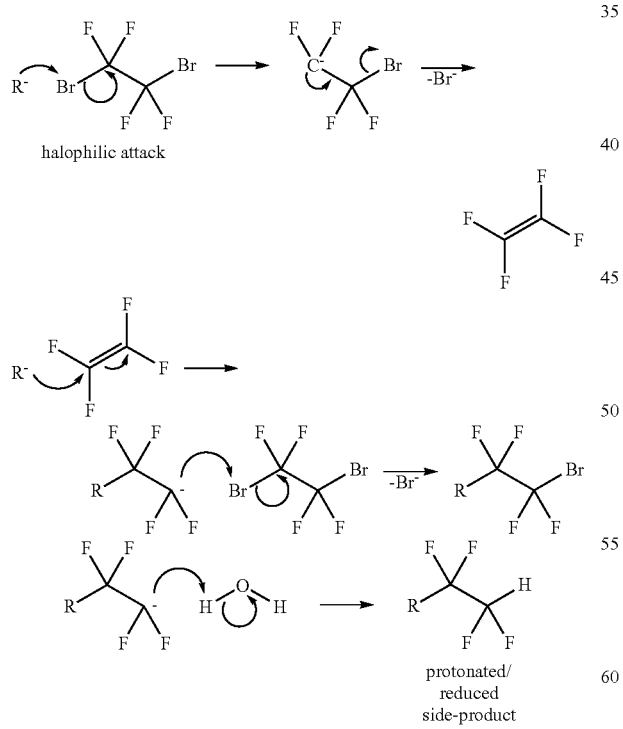

protonated/
reduced
side-product

In a second step, R—CF$_2$—CF$_2$—Br is reacted to R—CF$_2$—CF$_2$—SiPh$_x$(C$_1$-C$_3$-alkyl)$_{3-x}$ using Hal-SiPh$_x$(C$_1$-C$_3$-alkyl)$_{3-x}$ as reagent wherein the halogen (Hal) suitably is Cl.

In an alternative method avoiding Br—CF$_2$—CF$_2$—Br a nucleophile R—H is reacted with tetrafluoroethylene (CF$_2$=CF$_2$) in the presence of a catalyst, e.g. NaH/n-Bu4NI, to yield X—CF$_2$—CF$_2$—H that—in a second step—is reacted to X—CF$_2$—CF$_2$—SiPh$_x$(C$_1$-C$_3$-alkyl)$_{3-x}$ using Hal-SiPh$_x$(C$_1$-C$_3$-alkyl)$_{3-x}$ as reagent in the presence of a base.

X—CF$_2$—CF$_2$—SiPh$_x$(C$_1$-C$_3$-alkyl)$_{3-x}$ or its use in the preparation of hypervalent iodine-fluoroalkyl reagents and in the preparation of fluoroalkyl and fluoroalkylene compounds is also an object of the present invention.

In a final step, R—CF$_2$—CF$_2$—SiPh$_x$(C$_1$-C$_3$-alkyl)$_{3-x}$ is reacted with an "iodane" alcohol or acid such as

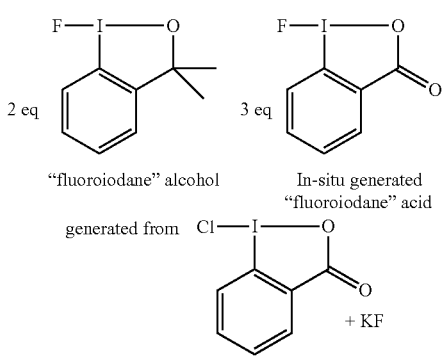

"fluoroiodane" alcohol     In-situ generated
                                      "fluoroiodane" acid generated from to yield

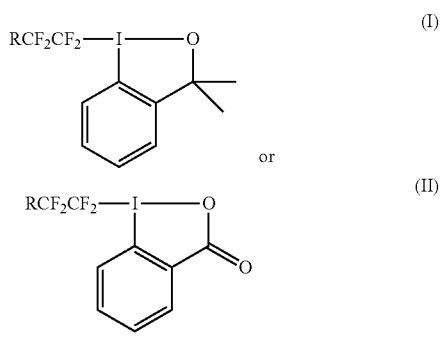

For the same or similar R groups, the compounds of formula (I) usually distinguish from the reagents of formula (II) in that those of formula (I) have better solubility and higher basics while those of formula (II) are the better oxidants.

Since R must be a nucleophile, it may be necessary to provide a desired group with a nucleophilic substituent such as —SH or —OH, possibly via a linker in order to retain the original features of the desired group. In this case R in compounds of formula (I) or formula (II) is "desired group-linker-nucleophilic substituent". In e.g. biological applications such desired groups can e.g. be fluorescent groups or biotin.

Some examples of compounds of formula (I) and/or formula (II) are azole-tetrafluoroethyl-based reagents, phenoxytetrafluoroethyl and thiophenoxytetrafluoroethyl-substituted reagents. These represent the families that can be most easily tuned and functionalized. Halogen or heteroatom substitution on the aromatic nuclei of fluoroalkylated moieties can provide additional vectors for further functionalization in carbon-carbon and carbon-heteroatom bond-forming reactions.

Some of such compounds are illustrated below:

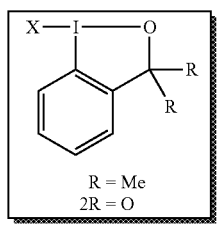

R = Me
2R = O

X =

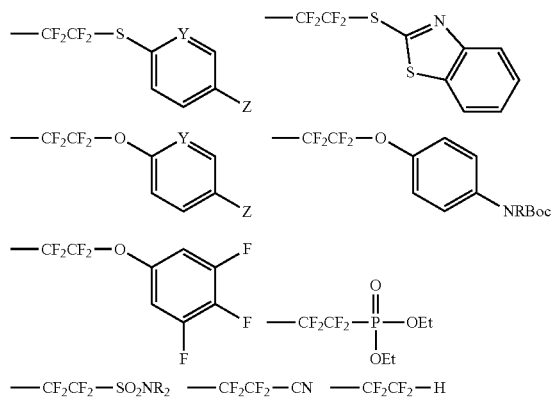

Y = CH, N
Z = H, Br

Compounds of formula (I) and/or formula (II) can be used for producing a broad variety of R—$CF_2$—$CF_2$-substituted compounds like compounds of all classes that have already been trifluoromethylated, e.g. by reacting compounds of formula (I) and/or compounds of formula (II) with reactive groups such as reactive groups of the following types:

sulfur centered nucleophiles, like —SH, carbon-centered nucleophiles, like silyl enolethers, silyl ketene imines and active methylene compounds, such as 1,3-dicarbonyl compounds, oxygen-centered nucleophiles, like —OH, hydroxylamines such as N-monosubstituted or preferably N,N-disubstituted hydroxylamines and sulfonic acids, nitrogen-centered nucleophiles, like cyclic aromatic heterocycles with at least 2 nitrogens, such as imidazoles, pyrazoles and triazole derivatives, phosphorous centered nucleophiles, like primary phosphines and secondary phosphines.

One preferred group to be reacted with the compounds of formula (I) or formula (II) are cysteins in any biological environment.

For example a cysteine group can be labelled with a fluorescent group in a very selective and close to quantitative manner according to the reaction scheme

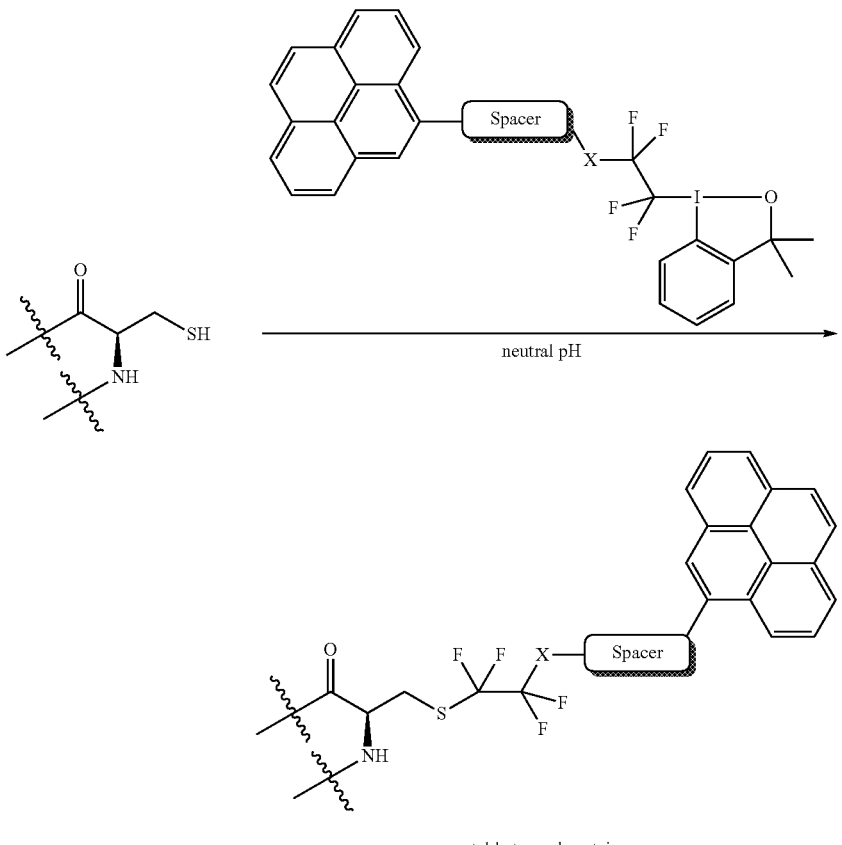

stable tagged cysteine

Such stable adduct can be used for the determination of reduced glutathione (GSH). In combination with HPLC fluorimetry GSH can be determined in blood plasma. The method allows the detection of free cysteine, homocystein, coenzyme A etc. in one single analysis.

In another application R comprises a biotinyl group

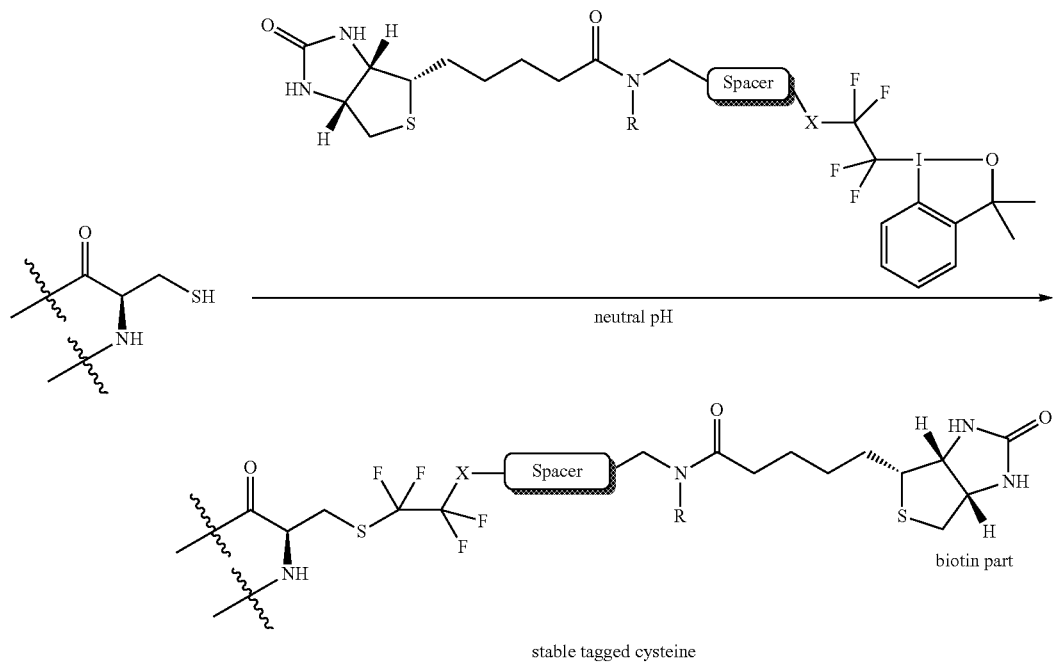

stable tagged cysteine

The introduction of the biotin moiety into cysteine comprising peptides and in cysteine rich domains allows use of Pull-Down Assays due to the high affinity of biotin to streptavidin.

BRIEF DESCRIPTION OF THE DRAWINGS

This description makes reference to the annexed drawings wherein:

FIG. 1 shows so far isolated compounds of formula (I) and formula (II). The numbers written under the reagents denote the isolated yields of successive steps in their syntheses (1. synthesis of XCF$_2$CF$_2$Br, 2. conversion of XCF$_2$CF$_2$Br to XCF$_2$CF$_2$TMS and 3. the final "Umpolung" step leading to the hypervalent iodine-CF$_2$CF$_2$X reagent.

MODES FOR CARRYING OUT THE INVENTION

One method for producing compounds of formula (I) and compounds of formula (II) is via the following synthetic approach (below R=Nu):

1. Bromotetrafluoroethylation

NuH+BrCF$_2$CF$_2$Br→NuCF$_2$CF$_2$Br

Nu=Nucleophile

2. Reduction/Trimethylsilylation $$\text{NuCF}_2\text{CF}_2\text{Br} \xrightarrow[\text{Me}_2\text{SiCl}]{\text{Reductant or metallating agent}} \text{NuCF}_2\text{CF}_2\text{SiMe}_2$$

3. Umpolung
   a) alcohol reagent:

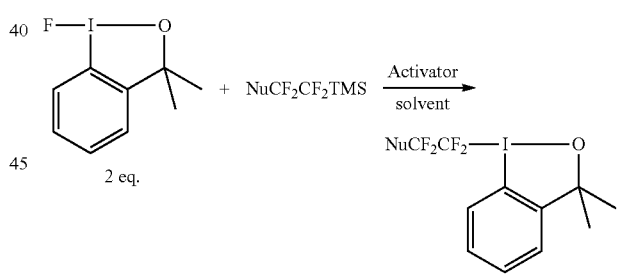

2 eq.

b) acid reagent:

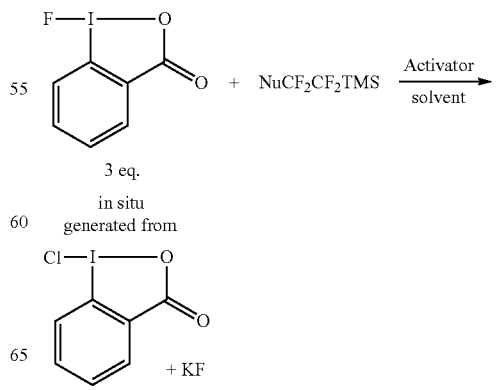

3 eq.
in situ generated from

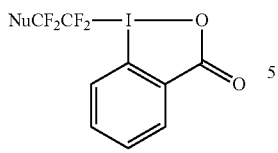

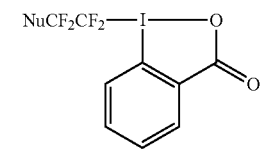

TBAT = tetrabutylammonium triphenyldifluorosilicate
r.t. = 20° C. to 25° C.

In preferred embodiments, the following more detailed reaction conditions are used:

1. Bromotetrafluoroethylation

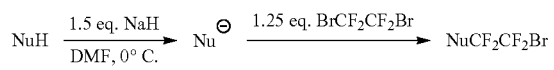

2. Reduction/Trimethylsilylation

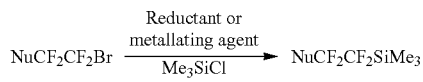

3. Umpolung
   a) alcohol reagent:

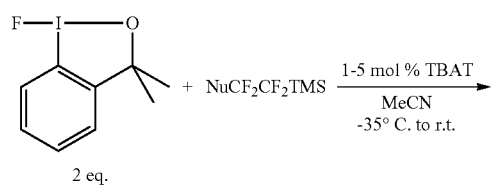

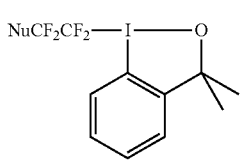

b) acid reagent:

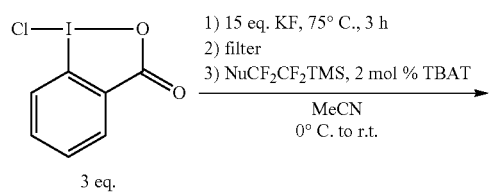

Suitable reducing or metallating agents/methods are e.g. metallic magnesium, metallic aluminum, metallic zinc, tris-dialkylaminophosphines, tetrakis-dialkylaminoethylenes, i-propylmagnesium chloride-lithium chloride complex, Grignard reagents, alkyl, alkenyl and aryl lithiums, and cathodic electroreduction.

Other activators that can be used are generally ate complexes of fluoride anion and an inorganic or organic Lewis acidic organic acceptor, sources of naked anhydrous fluoride anion, such as tetraalkylammonium fluorides, tetraalkylphosphonium or tetraarylphosphonium fluorides, cesium fluoride, combination of alkali metal fluorides and alkali metal chelators such as crown ethers n or related structures.

Solvents other than acetonitrile are THF, higher nitrile analogues of acetonitrile, halogenated aliphatic and aromatic solvents, tertiary carboxamides.

The Umpolung of the alcohol compound of formula (I) can be performed at temperatures up to 25° C. In general, however, it is performed at temperatures of at most 0° C. Often improved purity is obtained at temperatures significantly below 0° C. such as below −10° C. or even below −20° C. such as −35° C. Due to its lower reactivity, the Umpolung of the acid compound usually is performed at higher temperature, usually at temperatures from about 0° C. up to ambient temperature (rt), usually 20° C. to 25° C.

Experimental Part

In the following experimental part trimethylsilanes are used as $Ph_x(C_1-C_3-alkyl)_{3-x}$ silanes. Trimethylsilanesare preferred silanes because they are comparably cheap and readily available.

I. Synthesis of R—CF$_2$CF$_2$—X Reagents

I.1. Optimization of the Synthesis of Compound of Formula (I) with R=—SPh

Using PhSCF$_2$CF$_2$SiMe$_3$, an optimum protocol for smooth and high yielding Umpolung reaction was elaborated.

The comparison of the result of Umpolung of Ruppert-Prakash reagent with chloroiodane acid and fluoroiodane alcohol indicated that chloroiodane acid is not sufficiently reactive and that even in situ formation of fluoroiodane acid as mere intermediate results in poorer yields than starting from isolated fluoroiodane alcohol. The best result was obtained with the combined use of excess fluoroiodane alcohol and a well soluble fluoride source (e.g. tetrabutylammonium triphenyldifluorosilicate (TBAT)(see Table 1) as activator.

TABLE 1

Results of the Umpolung of PhSCF$_2$CF$_2$SiMe$_3$ with fluoroiodane alcohol

| entry | activator | equiv. of PhSCF$_2$CF$_2$SiMe$_3$ | equiv. fluoro-iodane alcohol | solvent | t [° C.] reaction time | yield[e] | scale |
|---|---|---|---|---|---|---|---|
| 1 | excess of spray dried KF | 1.2 | 1 eq. = 0.25M | MeCN | 0° C. to 25° C. 6 h | 22% (18%) | 100 mg |
| 2[a] | 10 mol % TBAT | 1 | 2 eq. = 0.25M | THF | −10° C. to 25° C. 3 h | (40%) | 100 mg |
| 3b | 10 mol % TBAT | 1 | 2 eq. = 0.33M | THF | 0° C. | 26% | 100 mg |
| 3[c] | 1 mol % TBAT | 1 | 2 eq. = 0.4M | MeCN | −20° C. to 0° C. 2 h | 69% (68%) | 100 mg |
| 4[d] | 1 mol % TBAT | 1 | 2 eq. = 0.4M | MeCN | −35° C. to 0° C. 1 h | 93% (85%) | 1 g |

[a]PhSCF$_2$CF$_2$SiMe$_3$ was added in three portions during 1 h.
bPhSCF$_2$CF$_2$SiMe$_3$ was added with syringe pump within 8 h.
[c]PhSCF$_2$CF$_2$SiMe$_3$ was added at once at −20° C.
[d]PhSCF$_2$CF$_2$SiMe$_3$ was added within 10 minutes
[e]the yields not in parenthesis are NMR yields measured with internal standard PhCF$_3$, those in parenthesis are isolated yields.
TBAT = tetrabutylammonium triphenyldifluorosilicate The worst result was obtained with KF. The Umpolung was slow and incomplete (entry 1). Switching to the use of isolated fluoroiodane alcohol in THF in combination with 10 mol % TBAT improved the yield to 40% (entry 2). During the conditions of entry 2, an instantaneous color change to orange was observed after the addition of the first portion of PhSCF$_2$CF$_2$SiMe$_3$ to the mixture of fluoroiodane alcohol and TBAT. This rapid color change might possibly be interpreted as an accompanying decomposition of PhSCF$_2$CF$_2$SiMe$_3$ in the presence of highly reactive fluoride activator. Therefore, in a next approach the reaction temperature was lowered to −20° C. and less activator was used (entry 3). This appeared to be a fruitful intervention leading to 69% NMR yield of PhS-I. Pleasingly, performing the reaction on a 1 g scale, lowering the reaction temperature to −35° C. and adding PhSCF$_2$CF$_2$SiMe$_3$ within 10 minutes gave 93% NMR yield of PhS-I. A quick TLC analysis of the reaction mixture revealed that the reaction was essentially complete in 5 minutes after the silane PhSCF$_2$CF$_2$SiMe$_3$ had been added.

These observations support the following hypothesis that, however, shall not be construed as limiting the invention in any way:

(i) highly soluble fluoride source is the best activator (ii) fluoroiodane alcohol is the best acceptor of the fluoroalkylated carbanion (iii) catalysis is mediated only by the fast dissolving fluoride such as TBAT throughout the whole catalytic Umpolung process ("pure fluoride catalysis") (This is astonishing since in a number of fluoridecatalyzed nucleophilic fluoroalkylations, for example additions of fluoroalkylated silanes to benzaldehydes, the catalytically relevant activator responsible for major part of the conversion is the intermediate alkoxide and not the fluoride.)

(iv) instability of activated fluoroalkylated silanes can be minimized by using excess of the acceptor fluoroiodane alcohol.

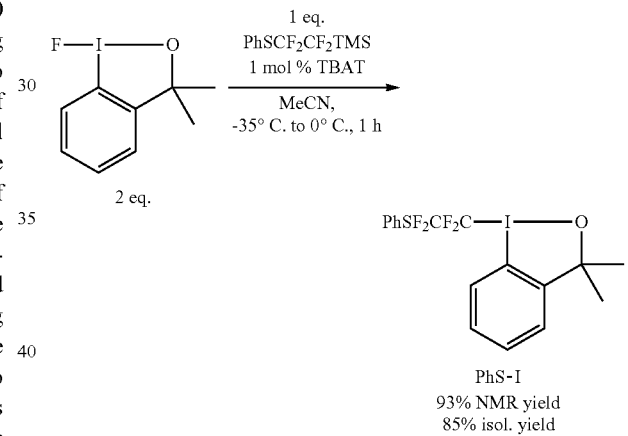

Optimized synthesis of PhS-I

PhS-I
93% NMR yield
85% isol. yield

I.2. Optimization of the Synthesis of PhS-II

Having optimized the synthesis of PhS-I, also the synthesis of the related "acid" reagent PhS-II was further investigated.

First the potential of acetoxyiodane acid as the precursor for synthesis of PhS-II was explored. However, the acetate of the acetoxyiodane acid proved to have insufficient activating power.

Thus, the poorly stable fluoroiodane acid was chosen. The fluoroiodane acid in pure form an only be obtained in solution, preferably as a solution in MeCN. Treatment of 2 equivalents of 1-chloro-benziodoxol-3-one (chloroiodane acid) with 10 equivalents of spray-dried KF in MeCN at 75° C. provided a suspension of KCl, KF and dissolved fluoroiodane acid. The solution of fluoroiodane acid was carefully canula-filtered under Ar from one into another Schlenk flash and treated with 10 mol % TBAT and 1 equivalent of PhSCF$_2$CF$_2$SiMe$_3$ at 5° C. Formation of PhS-II in 59% NMR yield together with 28% protodesilylation product of PhSCF$_2$CF$_2$SiMe$_3$ was observed.

In the next experiment, 3 equivalents of in-situ formed fluoroiodane acid together with 1 mol % TBAT was used.

First the Umpolung of PhSCF$_2$CF$_2$SiMe$_3$ was performed at 0° C., but even after 1 h, only low conversion of the silane PhSCF$_2$CF$_2$SiMe$_3$ was detected. After warming up to 20° C. to 25° C., much faster progress of the reaction was observed; within 3 h, the starting material could no longer be detected on TLC anymore. $^{19}$F NMR examination of the crude reaction mixture revealed formation of PhS-II in 60% NMR yield together with 17% PhSCF$_2$CF$_2$H. PhS-II could be then isolated by flash chromatography in 60% yield, with chromatographic behaviour similar to the related acid CF$_3$ reagent.

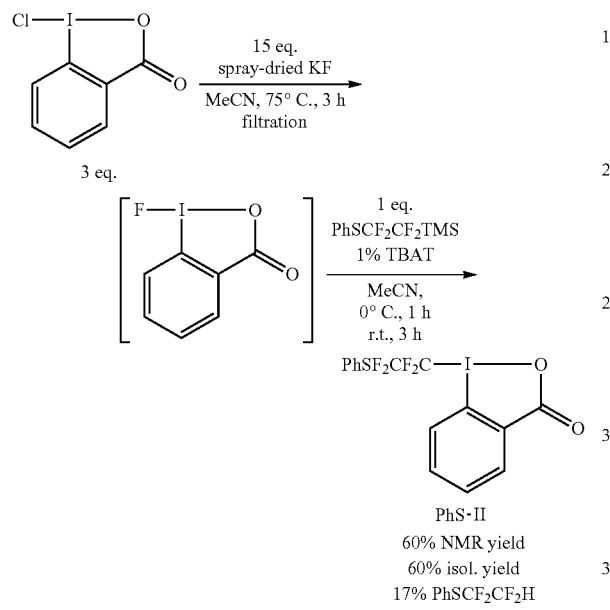

Preparation of PhSO$_2$CF$_2$CF$_2$-Acid-Reagent PhSO$_2$-II

When PhSO$_2$CF$_2$CF$_2$SiMe$_3$ was subjected to 3 equivalents of in-situ formed fluoroiodane acid in the presence of 1 mol % TBAT, formation of the desired reagent PhSO$_2$-II could be detected only in 8% NMR yield after 3 h at ambient temperature (20° C. to 25° C.). The lower nucleophilicity of the silane in combination with lower purity of PhSO$_2$CF$_2$CF$_2$SiMe$_3$ used is assumed to the reason of failure. The silane used in these experiments, namely, was contaminated with 15% protodesilylated material.

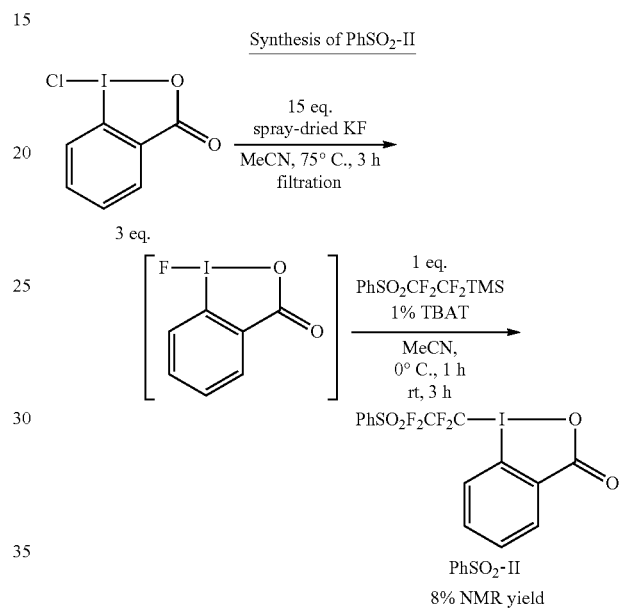

Preparation of PhSO$_2$CF$_2$CF$_2$-Alcohol-Reagent PhSO$_2$-I

The reaction of PhSO$_2$CF$_2$CF TMS with 2 equivalents of fluoroiodane alcohol in the presence of 1 mol % TBAT at −35° C. in MeCN gave 48% NMR yield of PhSO$_2$-I. Pure PhSO$_2$-I could be obtained in 32% isolated yield.

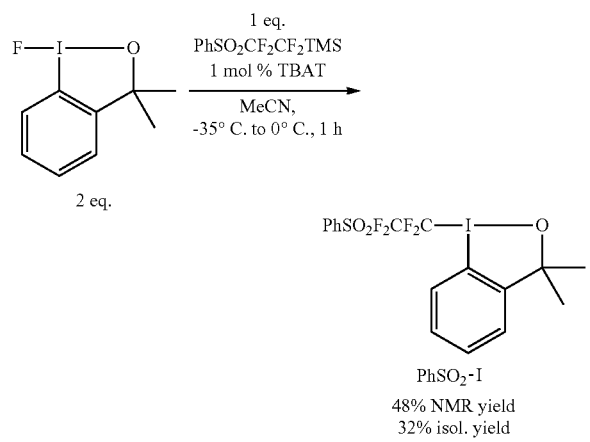

I. 4 Synthesis of 1-[(1,1,2,2-Tetrafluoro-2-Bromo]-1H-imidazole and Respective trimethylsilane Nitrogen-based heterocyclic functionalities are of high importance in medicinal chemistry and agrochemistry. Therefore compounds of formula (I) and formula (II) with R comprising nitrogen-containing heterocyclic groups are of high interest in these fields.

Im-I and Im-II were used as representatives of this class.

The synthesis of the desired reagents required access to the corresponding 1-[(1,1,2,2-Tetrafluoro-2-trimethylsilyl) ethyl]-1H-imidazole. Following the synthesis reported by Petko et al.[7], imidazole was deprotonated with 1.05 equivalents of sodium hydride in DMF and treated with 2 equivalents BrCF$_2$CF$_2$Br (see also [8]) in the presence of 2 mol % TBAT to give 1-[(1,1,2,2-Tetrafluoro-2-bromo]-1H-imidazole in 42% yield (Lit. 68% yield). In a second experiment, in order to need less dibromotetrafluoroethane, its excess was reduced to 1.5 equivalents and simultaneously the reactivity of the imidazolide anion was increased by increasing the amount of phase transfer catalyst (activator) to 7 mol %. Combination of these two adjustments provided 1-[(1,1,2,2-Tetrafluoro-2-bromo]-1H-imidazole in 68% yield which represents a certain improvement in comparison to the synthesis reported in the literature.

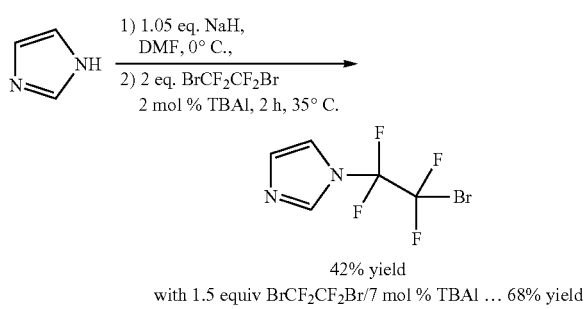

42% yield
with 1.5 equiv BrCF$_2$CF$_2$Br/7 mol % TBAI ... 68% yield

Synthesis of 1-[(1,1,2,2-Tetrafluoro-2-bromo]-1H-imidazole by Reaction of Imidazolyl Sodium with BrCF$_2$CF$_2$Br under PTC Catalysis Although the bromotetrafluoroethylation of imidazole formally represents a nucleophilic substitution, it actually comprises a combination of several elementary steps. The generally accepted mechanism is depicted in the Scheme below. The overall process is initiated by bromophilic attack of the nucleophile on BrCF$_2$CF$_2$Br, providing the brominated nucleophile and the highly unstable bromotetrafluoroethyl anion Int1 which quickly loses bromide anion to give the intermediate tetrafluoroethylene (Int2). Tetrafluoroethylene then behaves as the actual acceptor of the nucleophile, forming fluoroalkylated carbanion Int3. This carbanion is then finally brominated by a further bromophilic attack of BrCF$_2$CF$_2$Br, initiating a new reaction cycle with the release of new Int1.

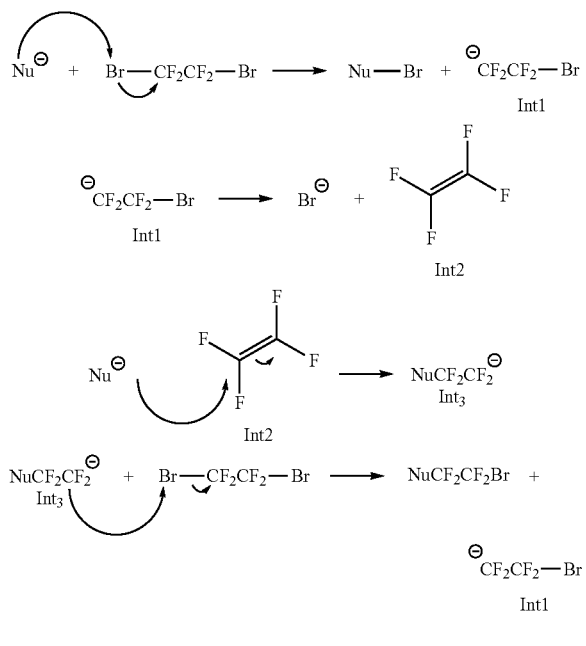

Mechanism of bromotetrafluoroalkylation of nucleophiles with BrCF$_2$CF$_2$Br

The next step in the synthesis of 1-[(1,1,2,2-Tetrafluoro-2-trimethylsilyl)ethyl]-1H-imidazole was a debrominative reductive silylation under Barbier conditions. 1-[(1,1,2,2-Tetrafluoro-2-bromo]-1H-imidazole was treated with 1.5 equivalents Mg grit and 4 equivalents of TMSCl in THF to provide the corresponding 1-[(1,1,2,2-Tetrafluoro-2-trimethylsilyl)ethyl]-1H-imidazole in 71% yield after Kugelrohr distillation. During the aqueous workup of the silane, care had to be taken to work under neutral conditions and in the cold, otherwise extensive protodesilylation of 1-[(1,1,2,2-Tetrafluoro-2-trimethylsilyl)ethyl]-1H-imidazole was observed.

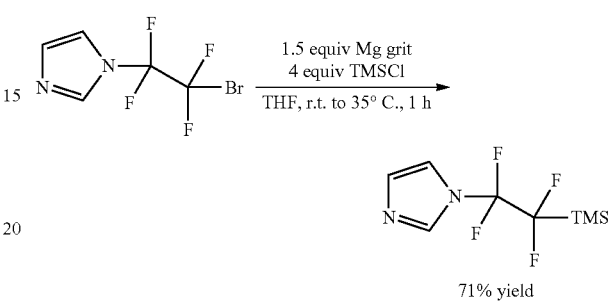

71% yield

Reductive silylation of 1-[(1,1,2,2-Tetrafluoro-2-bromo]-1H-Imidazole under Barbier Conditions I.5 Synthesis of Imidazole-I (Im-I)

1 equivalent of 1-[(1,1,2,2-Tetrafluoro-2-trimethylsilyl)ethyl]-1H-imidazole was treated with 2 equivalents of fluoroiodane alcohol in the presence of 1 mol % TBAT in acetonitrile at a temperature of −35° C. to 0° C. for 1 hour providing Im-I in 77-80% isolated yield. Similarly as in the case of synthesis of PhS-I, the Umpolung of 1-[(1,1,2,2-Tetrafluoro-2-trimethylsilyl)ethyl]-1H-imidazole with fluoroiodane alcohol was essentially finished within 10 minutes after addition of silane was complete (as evidenced by TLC analysis). Reagent Im-I was obtained as a viscous yellowish liquid that soon crystallized at ambient temperature (20° C. to 25° C.)

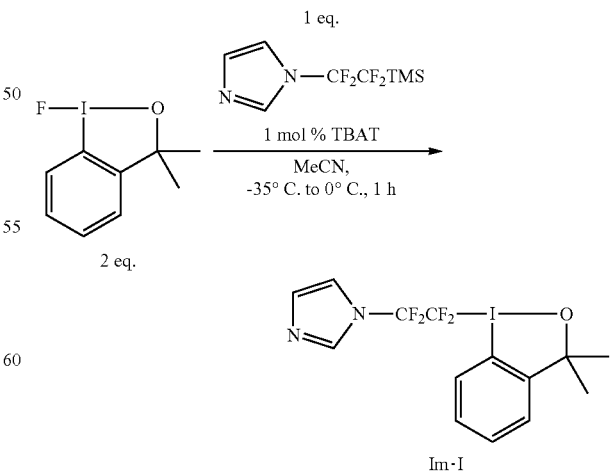

Im-I
77-80% isol. yield

Synthesis of "Alcohol-CF$_2$CF$_2$-Im Reagent"
imidazole-I (Im-I)

I.6 Synthesis of Imidazole-II (Im-II)

The synthesis of the related "acid-type" reagent Im-II was conducted along the lines of the previously optimized protocol. Reaction of 1 equivalent of 1-[(1,1,2,2-Tetrafluoro-2-trimethylsilyl)ethyl]-1H-imidazole with 3 equivalents of an in-situ formed fluoroiodane acid in the presence of 1 mol % TBAT gave Im-II in 66% NMR yield. The compound could be isolated by flash chromatography in 66% isolated yield.

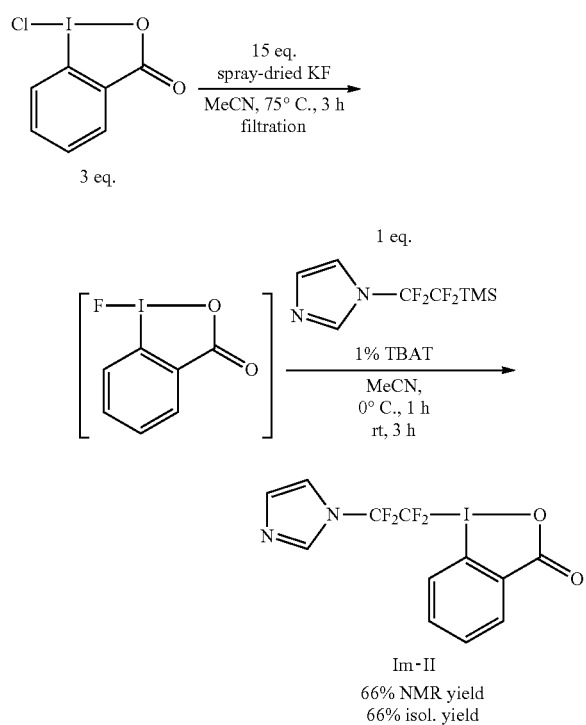

Synthesis of "Acid-CF$_2$CF$_2$-Im Reagent"
imidazole-II

According to the methods described above so far the compounds of formula (I) and formula (II) shown in FIG. 1 have been prepared in the indicated isolated yields.

In detail: The numbers written under the reagents denote the isolated yields of successive steps in their syntheses (1. synthesis of XCF$_2$CF$_2$Br, 2. conversion of XCF$_2$CF$_2$Br to XCF$_2$CF$_2$TMS and 3. the final "Umpolung" step leading to the hypervalent iodine-CF$_2$CF$_2$X reagent.

II. Solvent Dependence of $^{19}$F NMR Spectra of CF$_2$CF$_2$—X Reagents

When measuring the $^{19}$F NMR spectra of PhS-I in CDCl$_3$ on the one hand and in acetonitrile on the other hand an interesting phenomenon was observed. The crude reaction mixture showed in MeCN a well resolved pair of triplets at −83.1 ppm and −92.4 ppm. However, the isolated PhS-I re-dissolved in CDCl$_3$, gave one triplet at −82.2 ppm and a broad resonance at −89.9 ppm instead.

The same compound in d3-MeCN at ambient temperature (20° C. to 25° C.), gave again a clearly developed pair of triplets at −83.1 ppm and −92.4 ppm.

A similar solvent-dependent behaviour, only less pronounced, was observed for other reagents as well.

A not limiting interpretation of this behaviour might be as follows:

Reagent PhS-I is assumed to be in dynamic equilibrium between its cyclic and open iodonium-alkoxide form. It can be also conceived that the open iodonium-alkoxide form can coordinate the alkoxide moiety of a second molecule of PhS-I.[9] In a solvent with poor donor ability (represented by CDCl$_3$), the rate and extent of such dynamic processes is expected to be significant enough to lead to signal broadening. The more broadened $^{19}$F NMR resonance is assumed to correspond to the —CF$_2$-moiety directly attached to the hypervalent iodine center where the changes of electronic properties are most pronounced during these chemical exchange processes. Addition of solvent with good donor properties (represented by MeCN) is equivalent to addition of large excess of a ligand that effectively freezes the ligand exchange equilibria, whereby only the MeCN complex of PhS-I is observed (see below). A similar behaviour was observed for arylsulfur trifluorides where exchange of axial and equatorial fluorides was "frozen" by addition of diethyl ether, although the original nature of signal broadening is not exactly the same. [10]

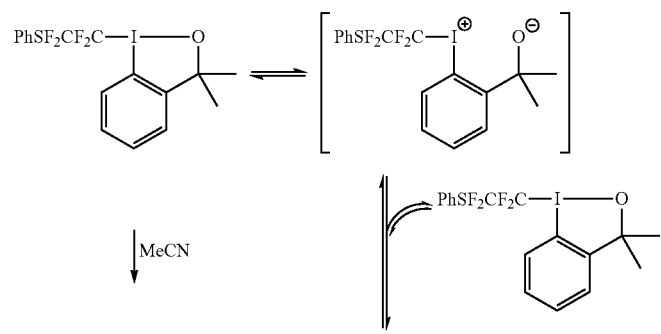

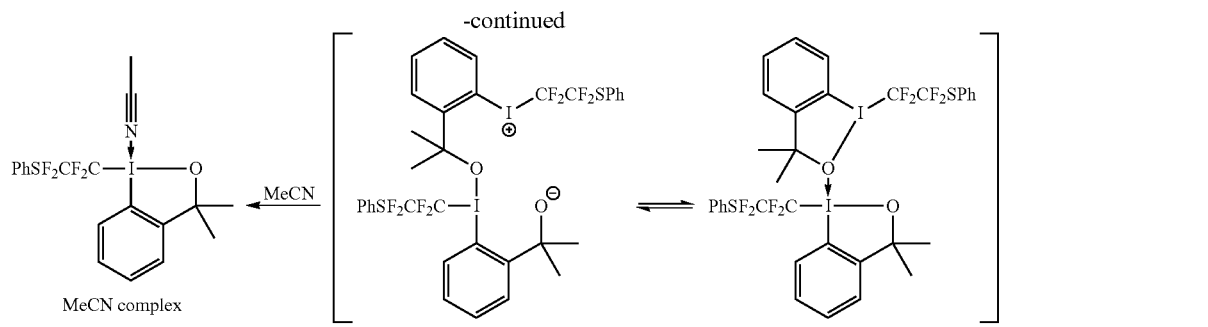

Suggested Coordination of Acetonitrile to PhS-I

Again this interpretation shall by no means be construed as limiting the scope of the present invention.

III. Storage Stability of the New $CF_2CF_2$—X Reagents

Only preliminary stability tests of reagents PhS-I, PhS-II, $PhSO_2$-I, Im-I and Im-II in the solid state and in solution in deuterated solvents ($CDCl_3$ and d3-MeCN) were performed.

All reagents could be handled for a few hours at room temperature without any decomposition. The well crystallizing reagent Im-II was stored at 25° C. for 5 days without decomposition.

However, as a solution in both $CDCl_3$ and d3-MeCN, significant decomposition (more than 50%) was detected after 24 h at room temperature, in standard borosilicate glass NMR tubes under air without exclusion of light. In the case of reagent PhS—I, severe stability problems were experienced. Partial decomposition could already be detected within 1 hour when using d3-MeCN that was not dry.

During storage of reagents PhS-I, PhS-II, $PhSO_2$—I, Im-I and Im-II for 4 months at −20° C. no decomposition was observed. It is therefore recommended to store the reagents in tightly sealed containers with exclusion of moisture at −20° C.

IV. Application of the Compounds of Formula (I) and Formula(II) in Formally Electrophilic Fluoroalkylation Reactions Based on the literature precedence of successful mild trifluoromethylation of thiols with alcohol CF3 reagent, [11] the reactivity of Im-I towards 4-chlorothiophenol was investigated. Upon addition of a solution of 1 equivalent of 4-chlorothiophenol to 1 equivalent of Im-I in DCM (dichloromethane) at −78° C., the reaction mixture instaneously turned yellowish-green. In the trifluoromethylation reaction of thiols, this greenish coloration was assumed to be caused by intermediary formation of charge transfer complex between the reagent and the thiol substrate. This could also be the case with Im-I. Within a minute, the yellowish-green solution turned colorless and a crystalline white solid formed. After warming up to ambient temperature (20° C. to 25° C.), an almost colorless solution was obtained. $^{19}F$ NMR analysis with internal standard revealed clean formation of the corresponding fluoroalkylated product in 93% yield (see Scheme below). Subsequent chromatographic isolation provided 1-[(1,1,2,2-Tetrafluoro-2-(4-chlorophenyl)]-1H-imidazole in 90% isolated yield as white needles.

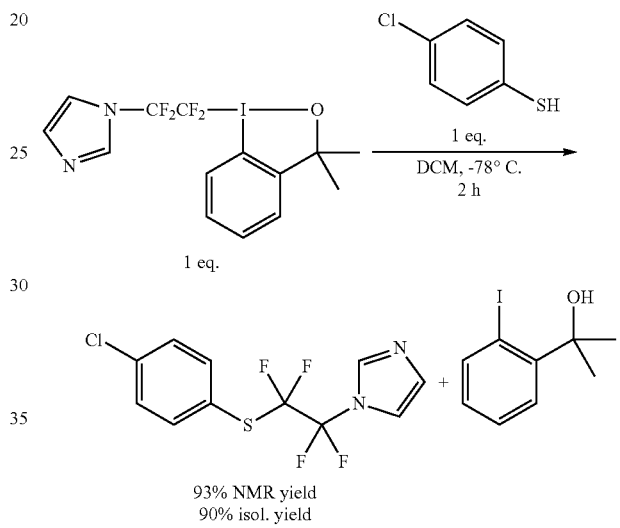

Fluoroalkylation of 4-chlorothiophenol with Imidazole-I

Another test reaction was the fluoroalkylation of N,N-disubstituted hydroxylamines.

Treatment of 1 equivalent of N,N-dibenzylhydroxylamine with 1 equivalent of PhS-I in DCM at ambient temperature (20° C. to 25° C.) gave after overnight reaction 70% NMR yield of the corresponding fluoroalkylated hydroxylamine. Isolation by flash chromatography yielded O-fluoroalkylated N,N-dibenzylhydroxylamine in 63% yield.

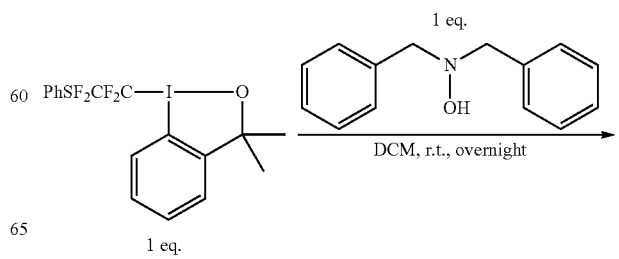

Fluoroalkylation of N,N-dibenzylhydroxylamine with PhS-I

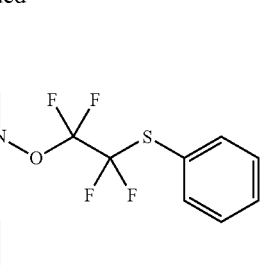

70% NMR yield
63% isol. yield

A further test reaction was fluoroalkylation of diphenylphosphine. Upon mixing 1 equivalent of diphenylphosphine with 1 equivalent of Im-I fast conversion to the corresponding fluoroalkylated diphenylphosphine was observed by $^{19}$F NMR. The NMR yield was 62%. Isolation has to be performed under non-oxidizing conditions.

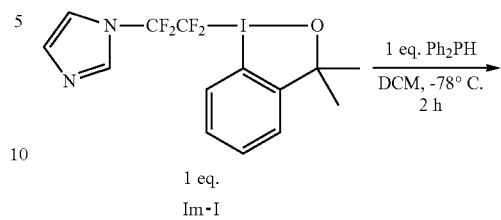

1 eq.
Im-I

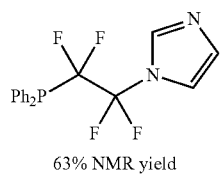

63% NMR yield

Reactions with further substrates have also already been examined. A list with reaction conditions is given in the following Table 2. The reagents are designated as in FIG. 1:

TABLE 2

| Substrate (type) | Reagent | Reaction |
|---|---|---|
| Bn$_2$-hydroxylamine (O) | A4 | Bn$_2$N-OH + A4 → Bn$_2$N-O-CF$_2$CF$_2$-SPh, DCM, r.t.; 20 h, ratio 1:1, 63% isolated |
| N-Boc-cysteine ester (S) | A1 | MeO-C(O)-CH(NHBoc)-CH$_2$-SH + A1 → product, DCM, -78° C.; 2 h, 1:1, 81% isolated |
| 4-Cl-thiophenol (S) | A2 | 4-Cl-C$_6$H$_4$-SH + A2 → product, DCM, -78° C.; 1 h, 1:1, 90% isolated |
| Diphenylphosphine (P) | A2 | Ph$_2$PH + A2 → product, DCM, -78° C.; 1 h, 1:1, isolated 63% |
| Skatole (C) | A2 | 3-methylindole + A2 → product, 10 mol. % Cu(OAc)$_2$, MeOH, r.t.; overnight, ratio 1:1.2, isolated 59% |

TABLE 2-continued

| Substrate (type) | Reagent | Reaction |
|---|---|---|
| β-Keto ester (C) | A4 | 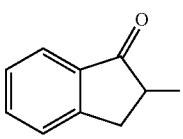 isolated 30% |
| β-Keto ester (C) | B4 | 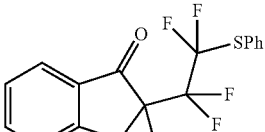 isolated 42% |
| Oxazolidinone 1 (C) | B4 | 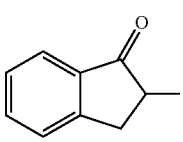 isolated 58%, 98:2 dr |
| Oxazolidinone 2 (C) | B4 | 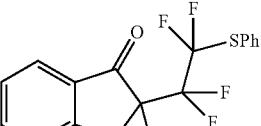 isolated 77%, >99:1 dr |
| 2-Mercapto-benzothiazol (S) | A | 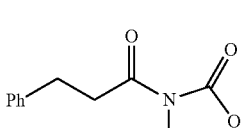 isolated 71% |

V. Conclusions

Fluoroiodane alcohols and fluoroiodane acids are the best Umpolung partners for fluoroalkylated silanes.

Pure fluoride catalysis with 1 mol % TBAT is able to mediate the very rapid Umpolung of nucleophilic fluoroalkylsilanes within minutes at −35° C.

Use of excess fluoroiodane alcohols and fluoroiodane acids helps to improve the yields of the desired hypervalent fluoroalkyl-iodine reagents (compounds of formula (I) and formula (II)).

VI. Useability of the Compounds of Formula (I) and Formula (II)

In the so far performed reactions "alcoholtype" reagents PhS-I and Im-I showed very promising potential, as thiols, N,N-disubstituted hydroxylamines, secondary phosphines and carbon centered nucleophiles proved to be receptive substrates in electrophilic fluoroalkylation. Further reactions wherein the compounds of the present invention are of interest are for example the diastereoselective fluoroalkylation of chiral Evans-type acyl oxazolidin-2-ones, fluoroalkylation of trimethylsilyl ketene acetals derived from lactones, enantioselective Cu-catalyzed fluoroalkylation of cyclic β-keto esters, fluoroalkylation of terminal acetylenes, alkenes and aryl- and alkenylboronic acids. Fluoroalkylation of heteroatom-centered nucleophiles like azoles and secondary phosphines is assumed to provide highly interesting ligand scaffolds applicable in homogeneous metal-catalyzed transformations.

The exceptional reactivity towards thiol substrates can be employed in selective tagging of cysteine residues in the context of highly complex peptide targets. For example, a reagent comprising a fluorescent moiety attached through a linker to the $CF_2CF_2$-moiety will serve as a double tag, suitable for both fluorimetric assay and NMR spectrometric detection.[12]

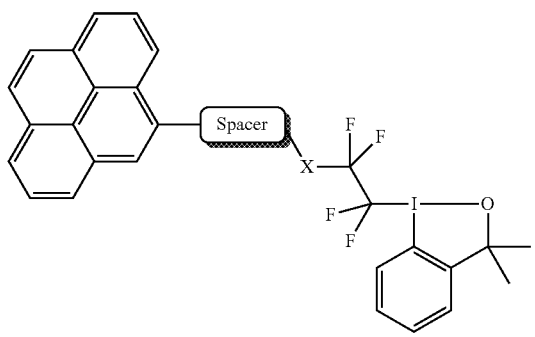

Pyrene Containing Reagent for Fluorescence Tagging of Cysteine Residues

Seen from a more general perspective, hypervalent fluoroalkyl-iodine reagents of formula (I) or formula (II) can function as highly thiol-selective carriers of a variety of moieties attached to the hypervalent iodine center.

From the life- and material science perspective, thanks to their excellent tunability, the compounds of formula (I) and formula(II) have broad application in discovery of new drugs, modification of existing lead structures and in the design of new functional materials (liquid crystals, fuel cell membranes, donor-acceptor molecular wires for solar electrochemical cells). For example, fluoroalkylation of existing drugs can improve some of their properties, for instance acidobasic behaviour or bioavailability. As an example of a modification with a compound of formula (I) or formula (II) Tenofovir may be mentioned. Tenofovir, marketed by the company Gilead Sciences, is an antiretroviral drug (reverse transcriptase inhibitor) effective against HIV1 and hepatitis B infections.

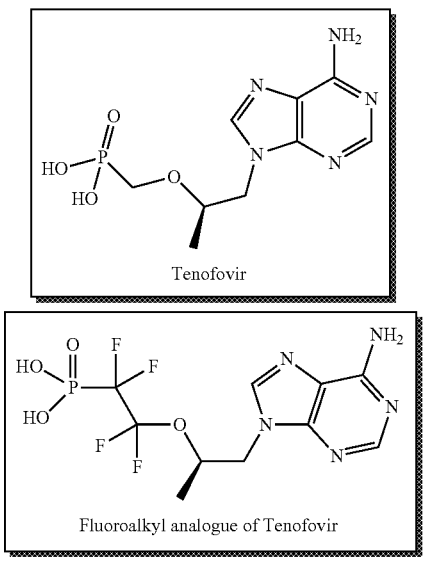

Tenofovir

Fluoroalkyl analogue of Tenofovir

Example for Use of a Tetrafluoroethylphosphonate Moiety in the Design of Modified Drugs While there are shown and described presently preferred embodiments of the invention, it is to be distinctly understood that the invention is not limited thereto but may be otherwise variously embodied and practiced within the scope of the following claims.

REFERENCES CITED

[1] a) P. Eisenberger, S. Gischig, A. Togni, *Chem. Eur. J.* 2006, 12, 2579-2586;
b) P. Eisenberger, ETH Zurich, Diss. No. 17371 (Zurich), 2007.
[2] a) J. Liu, C. Ni, F. Wang, J. Hu, *Tetrahedron Lett.* 2008, 49, 1605-1608;
b) C. Ni, J. Hu, *Tetrahedron Lett.* 2005, 46, 8273-8277.
[3] W. Zhang, J. Zhu, J. Hu, *Tetrahedron Lett.* 2008, 49, 5006-5008.
[4] Z. He, T. Luo, M. Hu, Y. Cao, J. Hu, *Angew. Chem. Int. Ed.* 2012, 51, 3944-3947.
[5] Z. He, M. Hu, T. Luo, L. Li, J. Hu, *Angew. Chem. Int. Ed.* 2012, 51, 11545-11547.
[6] Y. Li, A. Studer, *Angew. Chem. Int. Ed.* 2012, 51, 8221-8224.
[7] K. I. Petko, T. M. Sokolenko, A. V. Bezdudny, L. M. Yagupolskii, *J. Fluorine Chem.* 2005, 126, 1342-1346.
[8] W. Dmowski, *J. Fluorine Chem.* 2012, 142, 6-13.
[9] V. Zhdankin, in *Hypervalent Iodine Chemistry: Preparation, Structure and Synthetic Applications of Polyvalent Iodine Compounds*, John Wiley and Sons, 2013, pp. 21-143.
[10] T. Umemoto, R. P. Singh, Y. Xu, N. Saito, *J. Am. Chem. Soc.* 2010, 132, 18199-18205.
[11] I. Kieltsch, P. Eisenberger, A. Togni, *Angew. Chem. Int. Ed.* 2007, 46, 754-757.
[12] a) Y. Kim, S. O. Ho, N. R. Gassman, Y. Korlann, E. V. Landorf, F. R. Collart, S. Weiss, *Bioconjugate Chem.* 2008, 19, 786-791;
b) M. C. Puljung, W. N. Zagotta, in *Current Protocols in Protein Science*, John Wiley & Sons, Inc., 2001;
[13] S. Mizuta et al., *Org. Lett.* 2013, 15, 1250-1253;
[14] B. Zhang et al., *Angew. Chem. Int. Ed.* 2013, 52, 10792-10795;
[15] Carboni et al., *Org. Lett.* 2014, 16, 1240-1243;

The invention claimed is:
1. A compound of formula (I) or formula (II),

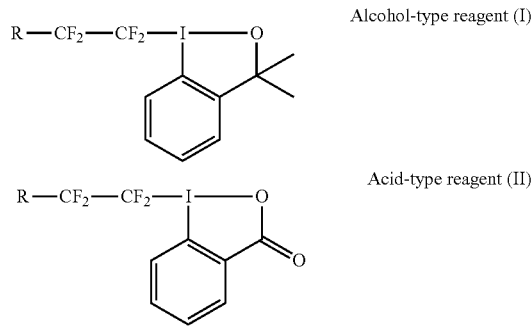

wherein R is selected from the group consisting of: unsubstituted or substituted imidazole, unsubstituted or substituted pyrazole, unsubstituted or substituted benzimidazole, unsubstituted or substituted thiophenol, unsubstituted or substituted hydroxypyridine, unsubstituted or substituted phenol, unsubstituted or substituted aminophenol, unsubstituted or substituted mercaptopyridine, unsubstituted or substituted 2-mercaptobenzothiazole, cyano, and diethylphosphite, and wherein R is substituted with a substituent independently from each other selected from the group consisting of: halogen, linear or branched, unsubstituted or halogen substituted C1 to C4 alkyl or C2 to C4 alkenyl or C2 to C4 alkynyl or C1 to C4 alkoxy or C1 to C4 alkyl carboxylate group, and an aliphatic linker coupled to pyrene or biotin wherein the aliphatic linker may optionally be halogen substituted.

2. The compound of claim 1, wherein R is selected from the group consisting of: imidazole, pyrazole, benzimidazole, hydroxypyridine, thiophenol, aminoalkylphenol, 4-methoxyphenol, ethyl-4-hydroxybenzoate, 4-bromophenols, pyridine-2-thiol, 2-mercaptobenzothiazoles, cyanide and diethylphosphite.

3. The compound of claim 1, wherein R is unsubstituted.

4. A method for the production of a compound of formula (I) or formula (II) of claim 1, comprising an Umpolung wherein (a) fluoroiodane alcohol is reacted with R—CF$_2$—CF$_2$—SiPh$_x$ (C$_1$-C$_3$-alkyl)$_{3-x}$, wherein x is 0 to 3, in the presence of at least one fluorine source as activator to give a compound of formula (I), or wherein (b) chloroiodane acid or fluoroiodane acid is reacted with R—CF$_2$—CF$_2$—SiPh$_x$(C$_1$-C$_3$-alkyl)$_{3-x}$, wherein x is 0 to 3, in the presence of at least one fluorine source as activator to give a compound of formula (II).

5. The method of claim 4, wherein (a) is performed with 2 eq. fluoroiodane alcohol per equivalent R—CF$_2$—CF$_2$—SiPh$_x$ (C$_1$-C$_3$-alkyl)$_{3-x}$, 1 to 5 mole % of one or more activators in a solvent at a temperature below 0° C., or wherein (b) is performed with 3 eq. chloroiodane alcohol per equivalent R—CF$_2$—CF$_2$—SiPh$_x$(C$_1$-C$_3$-alkyl)$_{3-x}$, one or more activators and about 2 mole % tetrabutylammonium tri-phenyldifluorosilicate (TBAT), in a solvent at a temperature between about 0° C. and 25°.

6. The method of claim 4, wherein R—CF$_2$—CF$_2$—SiPh$_x$ (C$_1$-C$_3$-alkyl)$_{3-x}$ is produced by a combined reduction and phenylalkylsilylation reaction or by a combined reduction and trimethylsilylation reaction of R—CF$_2$—CF$_2$—Br in the presence of a reducing or metallating agent, or applying cathodic electroreduction, and chlorophenylal-kylsilane.

7. The method of claim 6, wherein R—CF$_2$—CF$_2$—Br is produced by bromotetrafluoroethylation.

8. The method of claim 7, wherein the bromotetrafluoroethylation is performed by first reacting R—H with a hydride to form R~ and then reacting R$^-$ with Br—CF$_2$—CF$_2$—Br to form R—CF$_2$—CF$_2$—Br.

9. The method of claim 8, wherein the bromotetrafluoroethylation is performed by first reacting R—H (or Nu-H) with about 1.5 eq. of sodium hydride in a solvent to form R~ and then reacting R- with about 1.25 eq. Br—CF$_2$—CF$_2$—Br to form R—CF$_2$—CF$_2$—Br.

10. The method of claim 4, wherein R—CF$_2$—CF$_2$—SiPh$_x$ (C$_1$-C$_3$-alkyl)$_{3-x}$ is produced by reacting R—H with tetrafluoroethylene (CF$_2$=CF$_2$) in the presence of a catalyst to yield R—CF$_2$—CF$_2$—H that—in a second step—is reacted to R—CF$_2$—CF$_2$—SiPh$_x$ (C$_1$-C$_3$-alkyl)$_{3-x}$ using Hal-SiPh$_x$ (C$_1$-C$_3$-alkyl)$_{3-x}$ as reagent in the presence of a base.

11. A method for the production of a compound of formula (I) or (II)

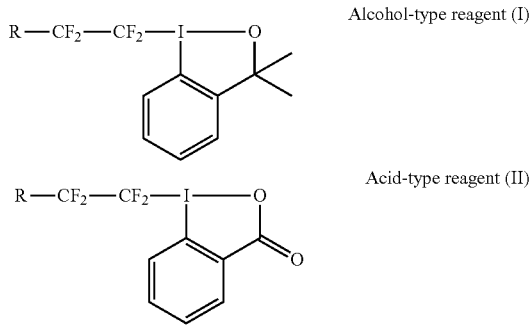

Alcohol-type reagent (I)

Acid-type reagent (II)

comprising:
reacting a fluoroiodane alcohol, chloroiodane acid or fluoroiodane acid with R—CF$_2$—CF$_2$—SiPh$_x$ (C$_1$-C$_3$-alkyl)$_{3-x}$, wherein R is selected from the group consisting of: unsubstituted or substituted imidazole, unsubstituted or substituted pyrazole, unsubstituted or substituted benzimidazole, unsubstituted or substituted thiophenol, unsubstituted or substituted hydroxypyridine, unsubstituted or substituted phenol, unsubstituted or substituted aminophenol, unsubstituted or substituted mercaptopyridine, unsubstituted or substituted 2-mercaptobenzothiazole, cyano, and diethylphosphite, wherein R is substituted with a substituent independently from each other selected from the group consisting of: halogen, linear or branched, unsubstituted or halogen substituted C1 to C4 alkyl or C2 to C4 alkenyl or C2 to C4 alkynyl or C1 to C4 alkoxy or C1 to C4 alkyl carboxylate group, and an aliphatic linker coupled to pyrene or biotin wherein the aliphatic linker may optionally be halogen substituted, and wherein X is 0 to 3.

12. The compound of claim 1, wherein R is selected from the group consisting of imidazole, pyrazole, benzimidazole, thiophenol, 4-methoxyphenol, ethyl-4-hydroxybenzoate, 4-bromophenol, pyridine-2-thiol, 4-(methylamino)phenol, 4-(ethylamino)phenol and 4-(propylamino)phenol.

13. The compound of claim 2, wherein the amino group of the unsubstituted or substituted aminophenol, aminoalkylphenol, 4-(methylamino)phenol, 4-(ethylamino)phenol or 4-(propylamino)phenol is protected by an acid-labile protecting group.

14. The method of claim 4, wherein the fluorine source as activator is selected from tetrabutylammonium triphenyldifluorosilicate (TBAT), tetraalkylammonium fluorides, tetraalkylphosphonium or tetraarylphosphonium fluorides, cesium fluoride, and crown ethers or related structures.

15. The method of claim 10, wherein R—CF$_2$—CF$_2$—SiMe$_3$ is produced by reacting R—H with tetrafluoroethylene (CF$_2$=CF$_2$) in the presence of a catalyst to yield R—CF$_2$—CF$_2$—H that—in a second step—is reacted to R—CF$_2$—CF$_2$—SiMe$_3$ using Hal-SiMe$_3$ as reagent in the presence of a base.

16. The method of claim 10, wherein the catalyst is NaH/n-Bu4NI.

17. The method of claim 10, wherein Hal-SiPh$_x$ (C$_1$-C$_3$-alkyl)$_{3-x}$ or Hal-SiMe$_3$ is ClSiPh$_x$ (C$_1$-C$_3$~alkyl)$_{3-x}$ or ClSiMe$_3$.

* * * * *